United States Patent
Alfattani

(10) Patent No.: US 10,842,899 B1
(45) Date of Patent: Nov. 24, 2020

(54) NON-CONTACT SANITIZER DISPENSER GLOVE

(71) Applicant: UMM AL-QURA UNIVERSITY, Mecca (SA)

(72) Inventor: Rami A. Alfattani, Mecca (SA)

(73) Assignee: UMM AL-QURA UNIVERSITY, Mecca (SA)

(*) Notice: Subject to any disclaimer, the term of this patent is extended or adjusted under 35 U.S.C. 154(b) by 0 days.

(21) Appl. No.: 16/997,295

(22) Filed: Aug. 19, 2020

(51) Int. Cl.
*A61L 2/22* (2006.01)
*A61L 2/26* (2006.01)
*A61M 35/00* (2006.01)
*B05B 11/04* (2006.01)
*B05B 11/00* (2006.01)

(52) U.S. Cl.
CPC ....... *A61L 2/22* (2013.01); *A61L 2/26* (2013.01); *B05B 11/0097* (2013.01); *B05B 11/048* (2013.01); *A61L 2202/15* (2013.01); *A61L 2202/16* (2013.01)

(58) Field of Classification Search
CPC .. A61M 35/10; A61L 2/22; A61L 2/26; A61L 2202/15; A61L 2202/16; B05B 11/048
See application file for complete search history.

(56) References Cited

U.S. PATENT DOCUMENTS

| | | | |
|---|---|---|---|
| 5,072,856 A | * | 12/1991 | Kimble ............. F41B 9/0078 222/78 |
| 5,169,251 A | | 12/1992 | Davis |
| 8,926,204 B1 | | 1/2015 | D'Ignazio |
| 9,783,978 B1 | | 10/2017 | Alqasimi et al. |
| 2007/0086828 A1 | | 4/2007 | Stewart |
| 2012/0282011 A1 | | 11/2012 | Francois |
| 2014/0157485 A1 | | 6/2014 | Tarlian, Jr. |

FOREIGN PATENT DOCUMENTS

| | | |
|---|---|---|
| CN | 107262405 A | 10/2017 |
| WO | WO 2016/056007 A2 | 4/2016 |
| WO | WO 2016/056007 A3 | 6/2016 |

OTHER PUBLICATIONS

"Coronavirus disease 2019 (COVID-19): Situation Report—59", World Health Organization, Mar. 19, 2020, 11 pages.

Xiaodong Zhang, et al., "Epidemiology of Covid-19", The New England Journal of Medicine, vol. 382, No. 19. May 7, 2020, pp. 1869-1870.

Zi Yue Zu, et al., "Coronavirus Disease 2019 (COVID-19): A Perspective from China", Radiology, vol. 296, No. 2, Aug. 2020, pp. E15-E25.

(Continued)

*Primary Examiner* — Kevin Joyner
(74) *Attorney, Agent, or Firm* — Oblon, McClelland, Maier & Neustadt, L.L.P.

(57) ABSTRACT

A sanitizer dispensing glove and a method of sanitizing an object using the glove. The sanitizer dispensing glove has a spray mechanism which is located on the palmar surface of a glove or mitt which is able to be operated to spray a sanitizer solution onto an object by a flexing or closing of a hand, finger, or other appendage wearing the glove without making contact with the object.

18 Claims, 6 Drawing Sheets

(56) References Cited

OTHER PUBLICATIONS

Yuxia Zhang, et al., "Hospital response to the COVID-19 outbreak: The experience in Shanghai, China", J Adv Nurs., vol. 76, 2020, pp. 1483-1485.

Zili Zhou, et al., "Effect of Gastrointestinal Symptoms in Patients With COVID-19", Gastroenterology, vol. 158, No. 8, Jun. 2020, pp. 2294-2297.

"The Epidemiological Characteristics of an Outbreak of 2019 Novel Coronavirus Diseases (COVID-19)—in China, 2020", The Novel Coronavirus Pneumonia Emergency Response Team, Chinese Center for Disease Control and Prevention, CCDC Weekly, vol. 2, No. 8, 2020, pp. 113-122.

Kit-San Yuen, et al., SARS-CoV-2 and COVID-19: The most important research questions, Cell & Bioscience, vol. 10, No. 40, 2020, pp. 1-5.

"Coronavirus and Surfaces: How Long Does COVID-19 Live on Surfaces?", WEBMD, https://www.webmd.com/lung/how-long-covid-19-lives-on-surfaces?print=true, 2020, 5 pages.

Daniel Lateş, et al., Fabrication Methods of Compliant Mechanisms, 10$^{th}$ International Conference Interdisciplinarity in Engineering, Inter-Eng, Procedia Engineering, vol. 181, 2017, pp. 221-225.

"Flexible Resin for Ergonomic Features", Formlabs Material Properties—Flexible: Photopolymer Resin for Form 2 3D Printers, Material Data Sheet, FLFLGR02, https://formlabs.com/materials/engineering/#flexible-resin, 2017, 2 pages.

Larry L. Howell, "Compliant Mechanisms", Ebook, New York: Wiley, vol. XVII, 2001, 459 pages (Abstract only).

Nicola M. Massy-Westropp, et al., "Hand Grip Strength: age and gender stratified normative data in a population-based study", BMC Research Notes, vol. 4, No. 127, 2011, pp. 1-5.

E. Shashi Menon, "Transmission Pipeline Calculations and Simulations Manual", Elsevier/Gulf Professional, vol. XII, 2015, 599 pages (Abstract only).

E. Loy Upp, et al., "Fluid Flow Measurement: A Practical Guide to Accurate Flow Measurement", Gulf Professional Publishing, https://www.elsevier.com/books/fluid-flow-measurement/upp/978-0-88415-758-8, 2$^{nd}$ Edition, Jan. 8, 2002, 296 pages (Abstract only).

\* cited by examiner

NON-CONTACT SANITIZER DISPENSER GLOVE

STATEMENT OF ACKNOWLEDGEMENT

The inventors acknowledge the support and funding provided by the Deanship of Scientific Research at Umm Al-Qura University through Grant Code #20-ENG-4-13-0002.

BACKGROUND OF THE INVENTION

Field of the Invention

The present disclosure relates to a sanitizer dispenser glove designed to allow for sanitizing an object without making contact with said object.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The spread of coronavirus (COVID-19) is now classified a pandemic and the whole world is affected. The pandemic will cause significant harm to the global economy and people all over the world will suffer as a result. Presently there are over eighteen million confirmed cases of coronavirus around the globe [World Health Organization, Coronavirus disease 2019 (COVID-19): situation report]. If the spread of COVID-19 continues the consequences may be catastrophic and take many years to overcome. Therefore, solutions to slow the spread of COVID-19 and any future pandemics are needed.

It has been confirmed that coronavirus can be spread through tactile contact, e.g., by contacting contaminated surfaces with hands [Zhang, X., Epidemiology of Covid-19. N Engl J Med, 2020. 382; and Zu, Z. Y., et al., Coronavirus Disease 2019 (COVID-19): A Perspective from China. Radiology, 2020: p. 200490]. When a person gets infected, symptoms may take 14 days to appear. During this time the infected person may participate in normal activities, unknowingly spreading the virus everywhere they went in this time frame [Zhang, Y., et al., Hospital response to the COVID-19 outbreak: the experience in Shanghai, China. J Adv Nurs, 2020; and Zhou, Z., et al., Effect of gastrointestinal symptoms on patients infected with COVID-19. Gastroenterology, 2020]. While going about normal activities, the surfaces that an infected individual comes into contact with have a high chance of becoming contaminated with the virus, thereby posing a risk of infection to others that contact the same surfaces [Zhonghua Liu Xing Bing Xue Za Zhi, The epidemiological characteristics of an outbreak of 2019 novel coronavirus diseases (COVID-19) in China, Chinese Journal of Epidemiology, 2020. 41(2): p. 145]. For this reason, it is important to sanitize all surfaces in an area with an active outbreak in order to minimize the risk of the infection spreading [Yuen, K. S., et al., SARS-CoV-2 and COVID-19: The most important research questions. Cell Biosci, 2020. 10: p. 40].

Sanitizing or disinfecting objects and surfaces that may harbor bacteria or viruses is a promising strategy for combating the spread of infectious diseases such as COVID-19, but it is inconvenient and labor intensive. For a healthcare worker, the need to deploy a sanitizer, dispense the sanitizer onto a surface, clean the surface, and then store the sanitizer is a time consuming process. Further, the sanitizing process may require the inefficient use of the sanitizing agent and/or other material (e.g. towels or cloths). Disposable gloves or cleaning cloths may need to be removed and safely discarded after each sanitizing event. For ordinary people going about daily tasks, it would be unreasonable to sanitize the large number of surfaces or objects they touch.

A sanitizer dispensing glove capable of non-contact sanitizing may allow a person to sanitize all the surfaces they touch quickly and conveniently. Further, a glove that dispenses sanitizer onto a surface or object before the surface or object comes into contact with the glove will additionally sanitize the glove after contact with the sanitizer-covered surface or object.

In view of the forgoing, one object of the present disclosure is to provide a sanitizer dispensing glove and a method of sanitizing an object without the need of making contact with said object.

SUMMARY OF THE INVENTION

The present disclosure relates to a sanitizer dispensing glove, comprising a spray mechanism attached to or disposed upon a palmar side of a glove or mitt, the spray mechanism comprising a pair of dispensing segments comprising a plurality of nozzles attached to, disposed upon, or formed from the material of the dispensing segments and one or more delivery tubes connected to the nozzles, and a central segment located between and flexibly connected to the pair of dispensing segments by joints comprising pressure arms, the central segment comprising a compressible chamber fluidly connected to the delivery tubes; a sanitizer solution reservoir; a replenishment tube, fluidly connected to the sanitizer solution reservoir and the compressible chamber, wherein the spray mechanism is capable of flexing from a relaxed state to a compressed state and relaxing from a compressed state to a relaxed state.

In some embodiments, the flexing of the spray mechanism from the relaxed state to the compressed state causes a compression of the compressible chamber which in turn causes an outflow of sanitizer solution housed in the compressible chamber into the delivery tubes and subsequently out through the nozzles as a spray and the relaxing of the spray mechanism from a compressed state to a relaxed state causes a decompression of the compressible chamber and subsequently an inflow of sanitizer solution from the sanitizer solution reservoir to the compressible chamber via the replenishment tube.

In some embodiments, the dispensing segments are substantially coplanar when in a relaxed state, having a dispensing segment angle, formed by the dispensing segments and central segment having the compressible chamber at the vertex of said angle, of 180 to 160°, and the dispensing segments are substantially non-coplanar in a compressed state, having a dispensing segment angle of less than 160°.

In some embodiments, the nozzles are oriented so as to provide a spray of sanitizer solution in a cone shape having a cone angle of 15 to 115°.

In some embodiments, a spray angle between a midpoint of the cone shape of the spray of sanitizer solution and the dispenser segment from which the spray originated is 30 to 90°.

In some embodiments, the sanitizer dispensing glove further comprises a replenishment one-way valve located between the compressible chamber and the replenishment tube.

In some embodiments, the replenishment one-way valve is oriented to allow an inflow of fluid from the replenishment tube into the compressible chamber and prevent an outflow of fluid from the compressible chamber into the replenishment tube.

In some embodiments, the sanitizer dispensing glove further comprises a delivery one-way valve located between the compressible chamber and each delivery tube.

In some embodiments, the delivery one-way valve is oriented to allow a flow of fluid from the compressible chamber to the delivery tube and prevent a backflow of fluid from the delivery tube to the compressible chamber.

In some embodiments, the spray mechanism is located on one or more finger areas of the palmar side of a glove or mitt.

In some embodiments, the spray mechanism is reversibly connected to the finger area or areas such that the spray mechanism may be removed, a portion of the glove may be replaced, and the spray mechanism may be reattached.

In some embodiments, the flexing of the spray mechanism and subsequent dispensing of sanitizer is caused by the flexing or closing of a hand, finger, or other appendage wearing the sanitizer dispensing glove.

In some embodiments, the sanitizer dispensing glove is configured to dispense sanitizer solution onto an object as a result of the action of grasping said object.

In some embodiments, the sanitizer dispensing glove is configured to dispense sanitizer solution onto an object without making contact with said object.

The present disclosure also relates to a method of sanitizing an object comprising spraying onto said object a sanitizer solution by flexing or closing a hand, finger, or other appendage wearing the sanitizer dispensing glove described above.

In some embodiments, the spraying occurs without any portion of the sanitizer dispensing glove making contact with the object.

In some embodiments, the sanitizer solution comprises a disinfectant.

In some embodiments, the method kills greater than 97.5% of microbes present on the object before sanitizing.

BRIEF DESCRIPTION OF THE DRAWINGS

FIG. 3A shows a relaxed state and FIG. 3B shows a compressed state;

DETAILED DESCRIPTION OF THE INVENTION

In the following description, it is understood that other embodiments may be utilized and structural and operational changes may be made without departure from the scope of the present embodiments disclosed herein.

As used herein, the terms "optional" or "optionally" means that the subsequently described event(s) can or cannot occur or the subsequently described component(s) may or may not be present (e.g., 0 wt. %).

Figure 1:
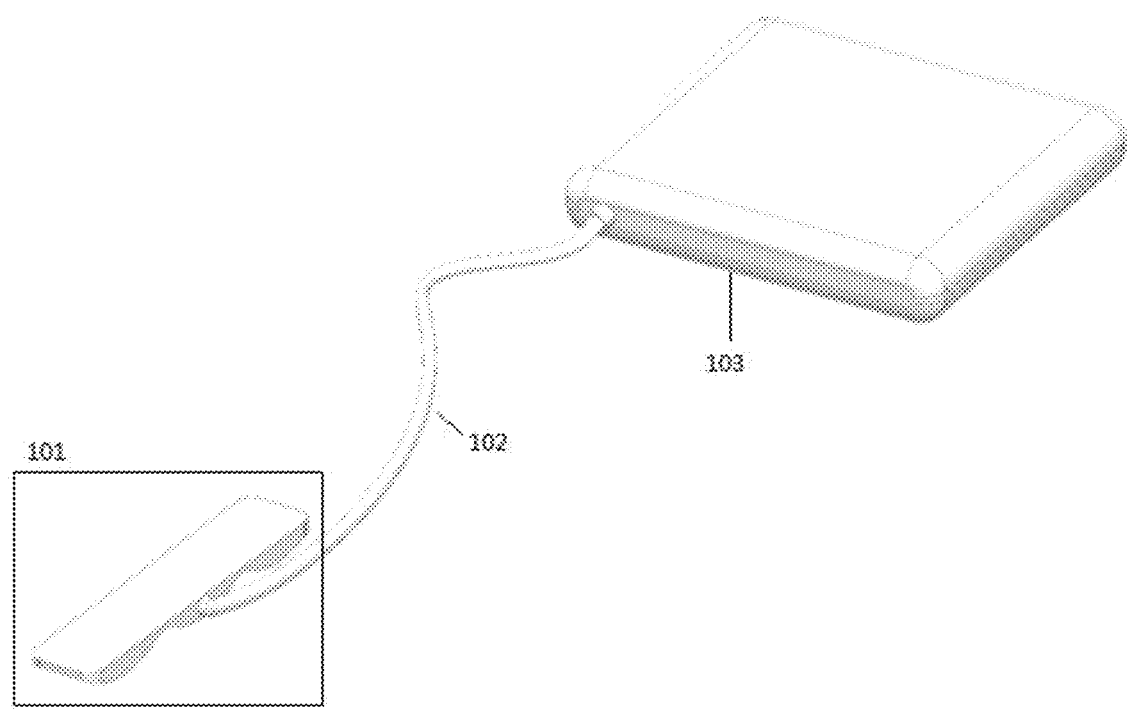
FIG. 1 shows the spray mechanism, the replenishment tube, and the sanitizer solution reservoir components of the sanitizer dispensing glove.

According to a first aspect, the present disclosure relates to a sanitizer dispensing glove. The sanitizer dispensing glove comprises, as shown in FIG. 1, a spray mechanism (101), a replenishment tube (102), and a sanitizer reservoir (103).

Figure 2:
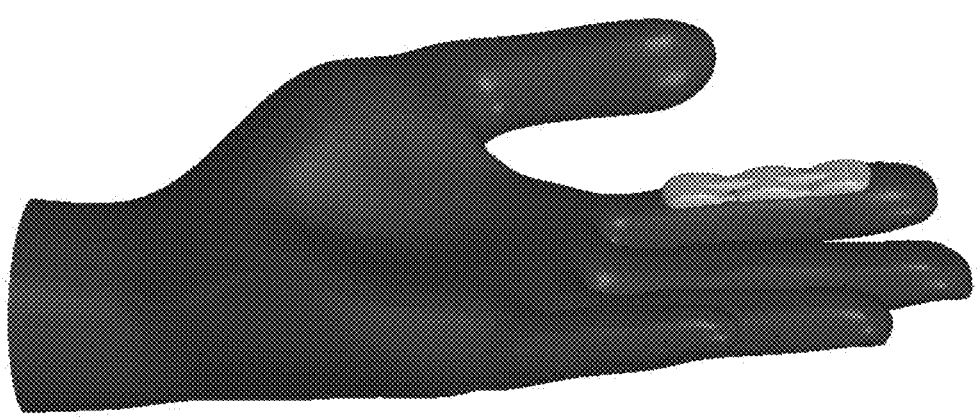
FIG. 2 shows a spray mechanism disposed upon a palmar surface of a glove.
Figure 3A:
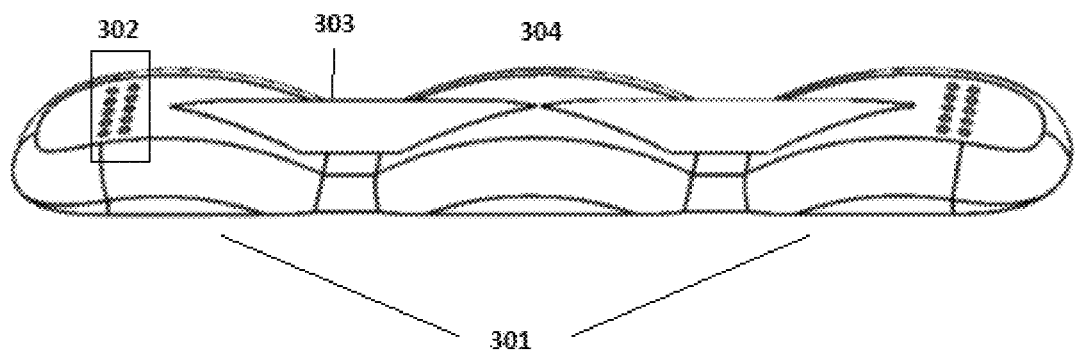
FIG. 3A-3B shows a spray mechanism where

The spray mechanism is attached to or disposed upon a palmar side of a glove or mitt, an example of which is shown in FIG. 2. The spray mechanism comprises a pair of dispensing segments and a central segment located between and flexibly connected to the pair of dispensing segments by joints. The dispensing segments comprise a plurality of nozzles attached to, disposed upon, or formed from the material of the dispensing segments and one or more delivery tubes connected to the nozzles. The central segment comprises a compressible chamber fluidly connected to the delivery tubes. An exemplary embodiment of the spray mechanism (shown in a relaxed state) is shown in FIG. 3A, showing the dispensing segments (301), the nozzles (302), the delivery tubes (303), and the central segment (304). In some embodiments, a single delivery tube is used per dispensing segment, the single delivery tube able to provide a flow of sanitizer solution to the plurality of nozzles located on said dispensing platform. In alternative embodiments, more than one delivery tube is used per dispensing segment, with each delivery tube able to provide a flow of sanitizer solution to one or more of the nozzles located on said dispensing platform.

Figure 3B:
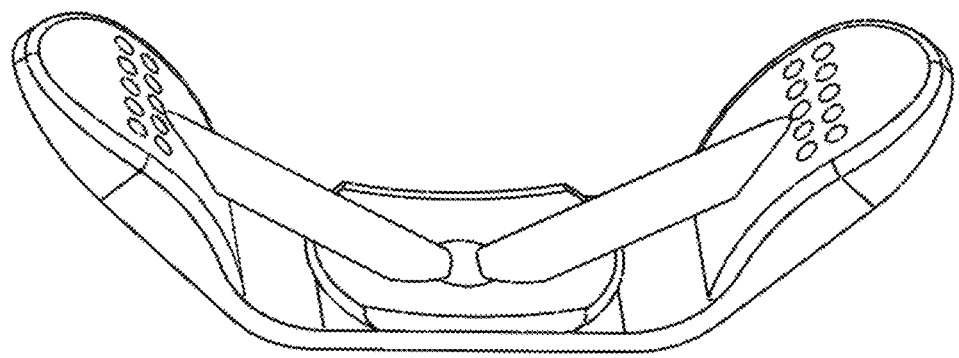

The spray mechanism is capable of flexing from a relaxed state to a compressed state and relaxing from a compressed state to a relaxed state. FIG. 3A shows the spray mechanism in the relaxed state, while FIG. 3B shows the spray mechanism in a compressed state. In some embodiments, the flexing of the spray mechanism from the relaxed state to the compressed state causes a compression of the compressible chamber. This compression in turn causes an outflow of sanitizer solution housed in the compressible chamber into the delivery tubes and subsequently out through the nozzles as a spray. In some embodiments, the relaxing of the spray mechanism from a compressed state to a relaxed state causes a decompression of the compressible chamber and subsequently an inflow of sanitizer solution from the sanitizer solution reservoir to the compressible chamber via the replenishment tube. In some embodiments, the dispensing segments are substantially coplanar when in a relaxed state, having a dispensing segment angle, formed by the dispensing segments and central segment having the compressible chamber at the vertex of said angle, of 180 to 160°, preferably 178 to 162°, preferably 176 to 164°, preferably 175 to 165°, preferably 174 to 166°. In some embodiments, the dispensing segment angle in the relaxed state is selected to allow a hand, finger, or other appendage wearing the sanitizer dispenser glove to adopt a natural relaxed state in which the hand, finger, or other appendage adopts an appendage angle of less than 180°, preferably less than 178°, preferably less than 176°, preferably less than 175°, preferably less than 174°, preferably less than 173°, preferably less than 172°. In some embodiments, the dispensing segments are substantially non-coplanar in a compressed state, having a dispensing segment angle of less than 160°, preferably less than 158°, preferably less than 156°, preferably less than 154°, preferably less than 152°, preferably less than 150°, preferably less than 148°, preferably less than 146°, preferably less than 144°, preferably less than 142°, preferably less than 140°. In some embodiments, the dispensing segment angle in the compressed state is selected to allow a user to operate the spray mechanism by a flexing of a hand, finger, or other appendage wearing the sanitizer dispenser glove. In some embodiments, said operation occurs after a sufficient displacement caused by the flexing. In some embodiments, the dispensing segment angle in the compressed state is selected to allow for a flexing of a hand, finger, or other appendage wearing the sanitizer dispenser glove that is of insufficient displacement to operate the spray mechanism.

Figure 4A:
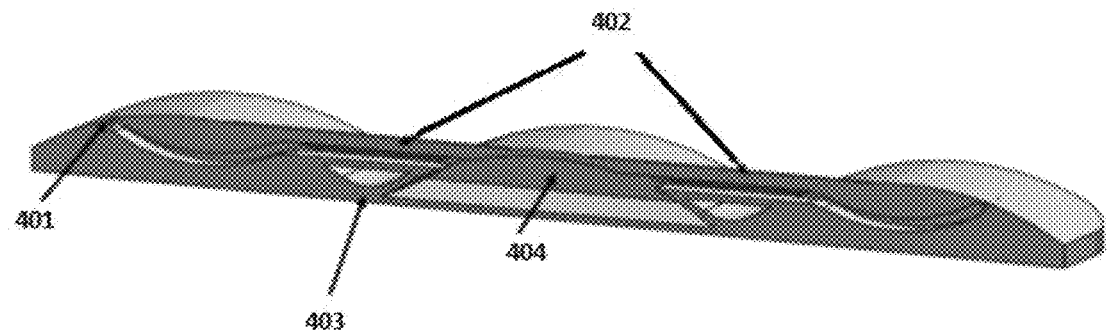
FIG. 4A-4B show cross-sections of a spray mechanism.
Figure 4B:
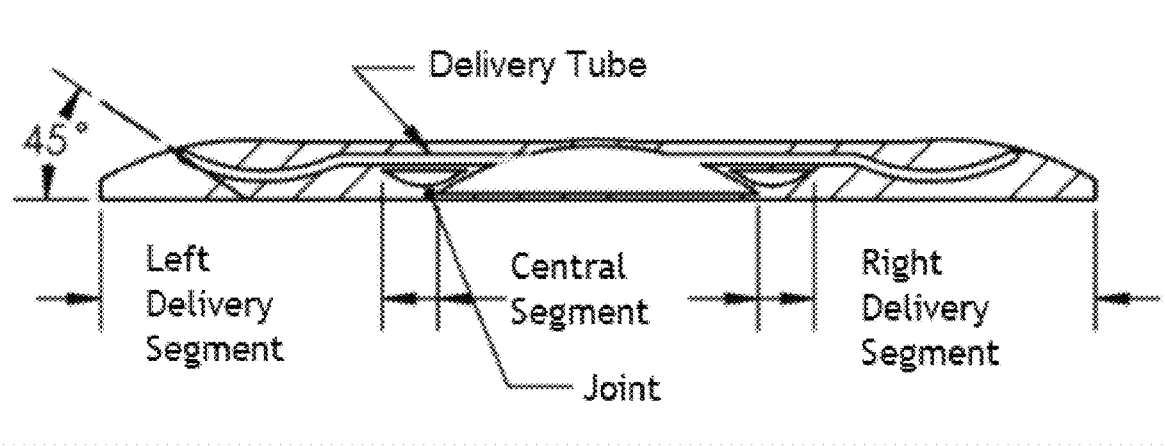

A cross-section of the spray mechanism is shown in FIG. 4A, depicting the nozzles (401), delivery tubes (402), joints (403), and compressible chamber (404). In some embodiments, the nozzles are separate objects or assemblies that are attached to or disposed upon the dispensing segments. In alternative embodiments, the nozzles are formed from the material of the dispensing segments. Such nozzles would be integrated into the dispensing segments. In some embodiments, the nozzles take the form of openings or orifices made into the dispensing segments. In preferred embodiments, the nozzles are located on the dispensing segments at an end of the dispensing platform that is opposite to an end of the dispensing platform attached to the central segment. In some embodiments, the nozzles are oriented so as to provide a spray of sanitizer solution in a cone shape. In some embodiments, the cone shape has a cone angle of 15 to 115°, preferably 30 to 110°, preferably 45 to 105°, preferably 75 to 100°, preferably 85 to 95°, preferably 87.5 to 92.5°, preferably 90°. In some embodiments, the nozzles are oriented to as to provide a spray angle between a midpoint of the cone shape of the spray of sanitizer solution and the dispenser segment from which the spray originated. In some embodiments, the spray angle is 30 to 90°, preferably 35 to 75°, preferably 40 to 60°, preferably 42.5 to 55°, preferably 45°. An exemplary embodiment is shown in FIG. 4B.

In general, the nozzles may be of any suitable nozzle design known to one of ordinary skill in the art. In preferred embodiments, the nozzles are single-fluid nozzles. Examples of single-fluid nozzles are orifice nozzles, shaped orifice nozzles, surface impingement nozzles, pressure swirl nozzles, solid cone nozzles, hollow cone nozzles, and fan nozzles. In preferred embodiments, the nozzles are solid cone nozzles. Solid cone nozzles provide a spray in the form of a filled, solid cone such that the filled, solid cone has a circular or elliptical cross section in which the interior of the circular or elliptical cross section contains spray fluid. Such a spray pattern is in contrast to hollow cone nozzles, which provide a similarly-shaped spray in which only a perimeter of the circular or elliptical cross section contains spray fluid. For examples of nozzles see US20200004153 and US20190388910A1

Figure 5:
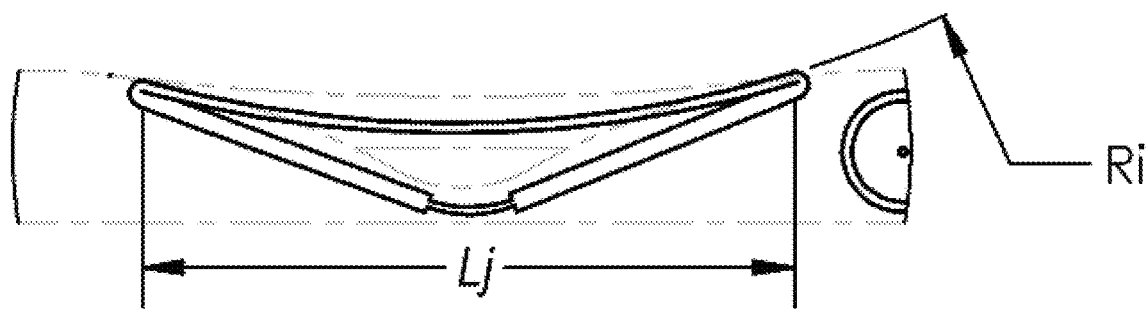
FIG. 5 shows a schematic of the joints.

In some embodiments, the joints are compliant mechanisms. Compliant mechanisms are flexible mechanisms that achieve force and motion transmission through elastic body deformation. A compliant mechanism gains some or all of its motion from the relative flexibility of its members rather than from rigid-body joints alone. In some embodiments, the joints comprise a living hinge. A living hinge is a thin flexible hinge (also known as a flexure bearing) made from the same material as the two rigid pieces it connects. It is typically thinned, scored, or cut to allow the rigid pieces (i.e. the dispensing segment and central segment) to bend along the line of the hinge. A living hinge is considered a type of compliant mechanism. In some embodiments, the joints comprise pressure arms. The pressure arms are rigid arms or members which contact the compressible chamber and provide a compressive force to the compressible chamber in the compressed state. In some embodiments, the pressure arms are formed from the delivery tubes. In alternative embodiments, the pressure arms are hollow. In such embodiments, the delivery tubes pass through an interior void of the pressure arms. In some embodiments, the joints comprise a pressure arm and a small-pivot flexural. An exemplary embodiment of the joints is shown in FIG. 5. In some embodiments, the joint is returned from a flexed state to a relaxed state by a restoring force. In some embodiments, the restoring force is provided by the material of the compliant mechanism. In alternative embodiments, the restoring force is provided by the pressure arms or a deformation thereof. The deformation of either the living hinge or the pressure arms can be considered to be acting against a flexural stiffness of the material of the pressure arms or living hinge. The flexural stiffness must be acted against for flex the joint from a relaxed state to a compressed state. In the context of the present invention, the force acting against the flexural stiffness is provided by the hand, finger, or other appendage of a user donning the sanitizer dispensing glove. In preferred embodiments, the joint is designed such that the flexural stiffness of the living hinge or pressure arms is sufficient to restore the spray mechanism from the compressed state to the relaxed state.

In some embodiments, the pressure harms have a hollow semicircular cross section. In such embodiments, a stiffness property of the hollow semicircular cross section dominates or dictates an overall stiffness property of the spray mechanism. In such embodiments, the overall stiffness property of the spray mechanism is approximated by the stiffness property of the hollow semicircular cross section. Such an approximation The hollow cross section of the pressure arms allow the delivery tubes to pass through them and transfer sanitizer solution from the central segment to the nozzle when the compressible chamber is compressed. As the left and right segments move, the rigidity of pressure arm causes it to press on the compressible chamber and push out and dispense the sanitizer solution. Once the pressure arm presses all the way on the central segment and reaches the base, the pressure arm will buckle if the load keeps increasing. At this stage, the pressure arm is fixed at the right end and the load increasing at the other end.

In some embodiments in which the joints are compliant mechanisms, the design and action of the joints can be modeled as slider mechanism. Such modeling may be achieved by considering the symmetry of the fully compliant mechanism using Pseudo-Rigid-Body Model. The stiffness of the pressure tube link is modeled as torsional springs that are placed on the link. The link has initial curve characteristic that guided the deflection path. The pressure arm and the small-pivot flexural are modeled using Pseudo-rigid-body model (PRBM) approach. The PRBM was early developed by Howell to approximate the large deflection of compliant beams [Howell, L. L., Compliant mechanisms. 2001, New York: Wiley. xvii, 459; incorporated herein by reference]. Different types of loadings and conditions can have different type of PRBM models. In some embodiments, the pressure arm link is considered as pinned-pinned beam with grip force at its end.

Figure 6:
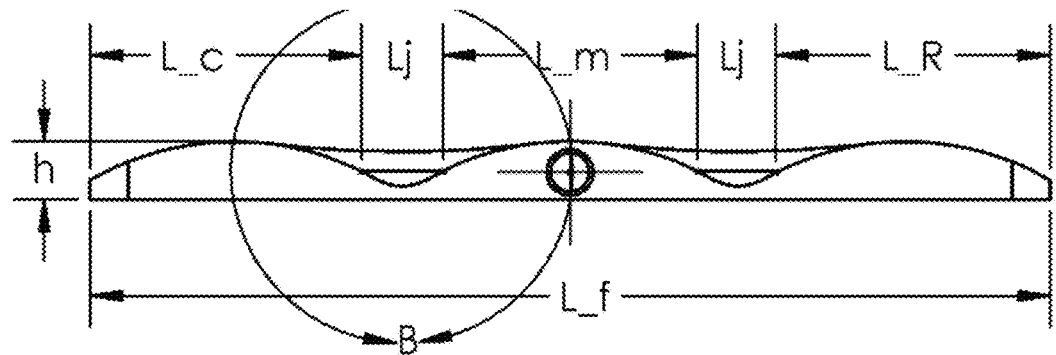
FIG. 6 shows a schematic of the spray mechanism.
Figure 7:
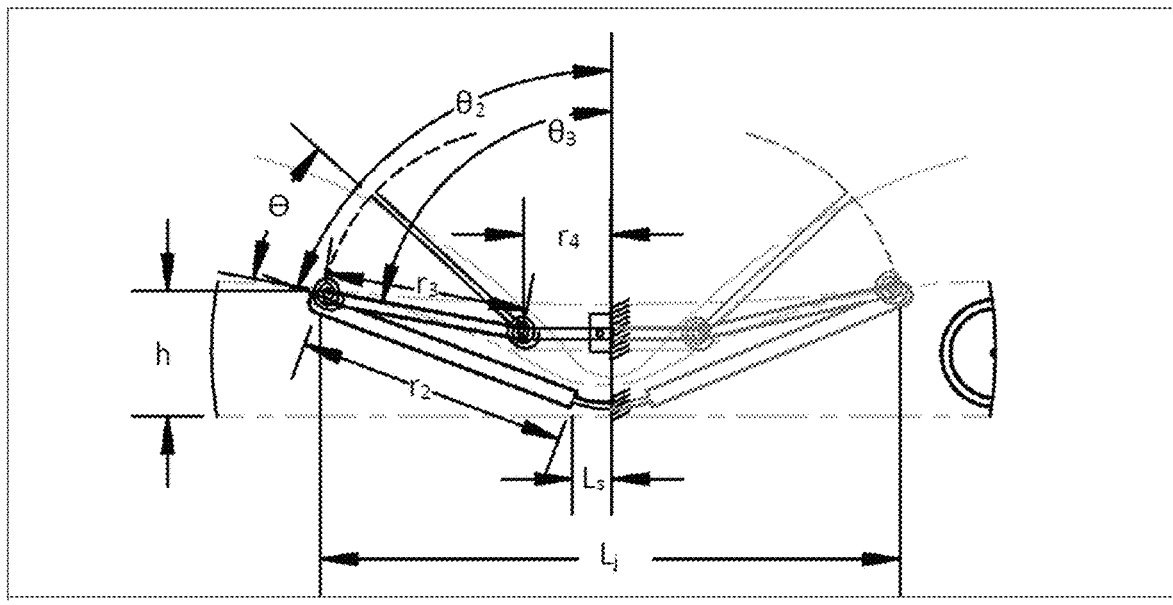
FIG. 7 shows a depiction of the model and variables used in the pseudo-rigid-body model of the action of the joint.
Figure 8:
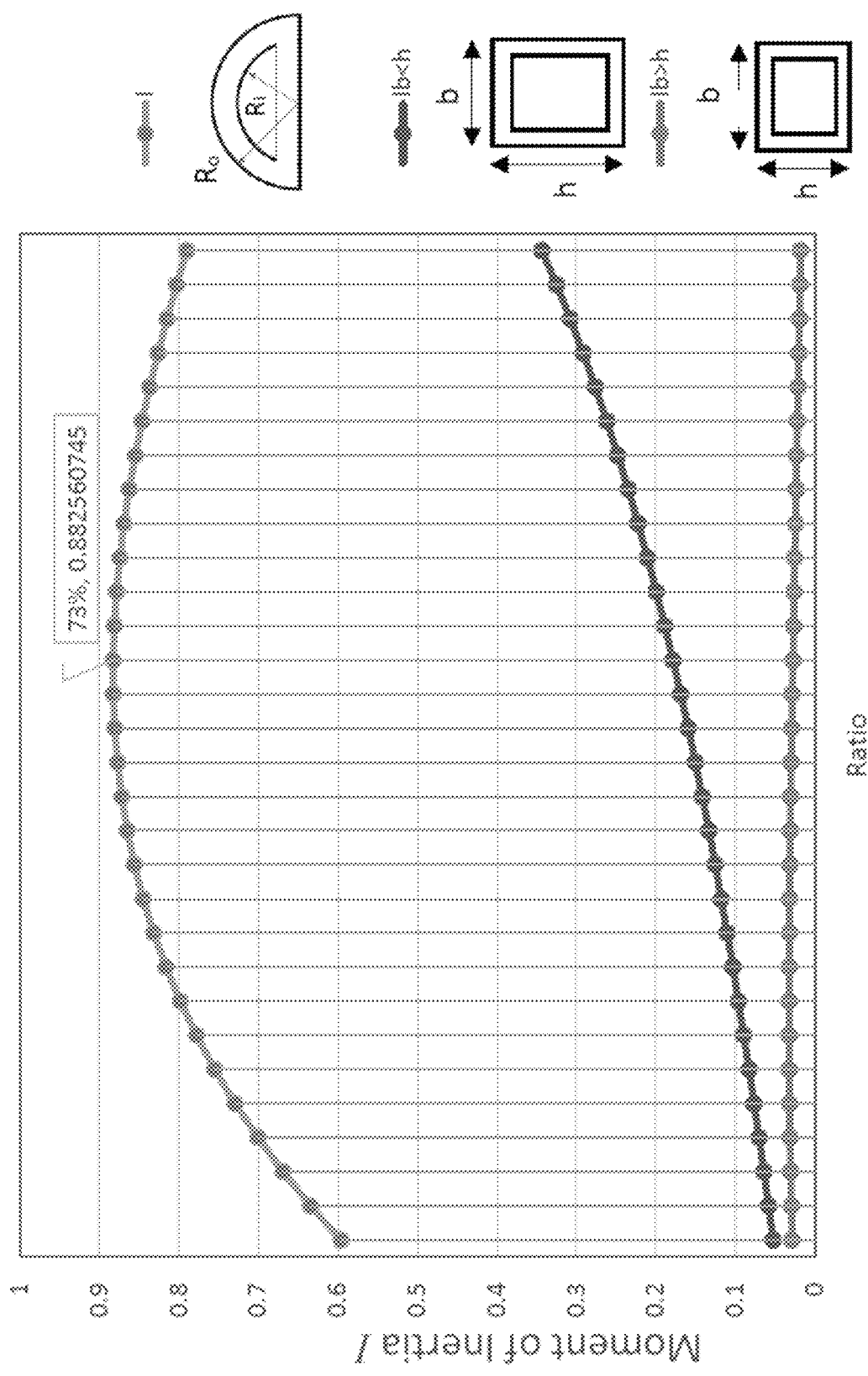
FIG. 8 shows a plot of the moment of inertia vs the ratio of inner dimension and outer dimension for various shapes.

In some embodiments, the compliant mechanism may be constructed or modeled with a rigid-body replacement synthesis approach. The modeling approach approximates the compliant links as two rigid links joined by torsional springs. Such a model may simplify the necessary computation versus other models. The torsional spring have a stiffness coefficient K denied by the material properties is assigned at the calculated position that represents the resistance as the link deflecting. The angle of deflection of pseudo-rigid-link is referred to as the angle of the pseudo-rigid-body Θ. This pseudo-rigid body model (PRBM) considers homogeneous material properties. The links lengths of the fully compliant mechanism are specified as function of the length of the wearer's fingers ($L_f$). The equations representing this model are pseudo-rigid-body as well as the variables that go into the model (see FIG. 5, FIG. 6, and FIG. 7) are shown below:

$$L_c = L_R = L_m = 0.3 L_f \quad (1)$$

$$L_j = 0.05 L_f \quad (2)$$

$$h = 0.1 L_f \quad (3)$$

$$r_2 = \sqrt{h^2 + \left(\frac{L_c + L_j}{2}\right)^2} \quad (4)$$

$$r_3 = \frac{L_c + L_j}{2} \quad (5)$$

$$r_4 = \frac{L_j}{2} \quad (6)$$

$$r_1 = r_3 \cos\theta_3 + r_2 \cos\theta_3 \quad (7)$$

$$\theta_3 = \operatorname{asin}\left(\frac{r_4 - r_3 \sin\theta_2}{r_3}\right) \quad (8)$$

$$\theta_{2o} = \frac{\pi}{2} - \operatorname{acos}\frac{h}{r_2} \quad (9)$$

$$F\alpha\sin\theta_2 = K_2((1+H)(\theta_2 - \theta_{2o}) - (1+2H)(\theta_3 - \theta_{3o})) - K(\theta_2 - \theta_{2o}) \quad (10)$$

$$K_2 = \frac{2\gamma k_\theta E I_3}{r_3} \quad (11)$$

$$K_1 = \frac{EI_s}{L_s}, \quad L_s = \frac{0.15 L_j}{2}, \quad I_s = \frac{wt^3}{12} \quad (12)$$

$$H = \frac{r_2 \cos\theta_2}{r_3 \cos\theta_3} \quad (13)$$

Where α is equal to $r_2$, $k_\Theta$ is a stiffness coefficient that equals 2.65 as recommended by Howell [Howell, L. L., Compliant mechanisms. 2001, New York: Wiley. xvii, 459], and t is the thickness of the small pivot flexural that equals 10% of the width. The width w of the spray mechanism equals 10% of the total length of the spray mechanism. The vertex angle $\theta_2$ is the range of left segments' movement after reaching the base which will be detected from the movement of fingers. Equation 10 is the governor equation of the mechanism. The average grip force is known from [Massy-Westropp, N. M., et al., Hand Grip Strength: age and gender stratified normative data in a population-based study. BMC research notes, 2011. 4(1): p. 127] and can be estimated based on the gender and age of the user. The output from equation 10 is the geometry schematic which will define the dimensions of the pressure arm based on the moment of inertia of the cross section $I_3$:

$$I_3 = \frac{9\pi^2 - 64}{72\pi} R_0^4 (1-\xi) + 2R_0^4 \xi (1-\xi) \quad (14)$$

Where $R_0$ is the outer radius and ξ is the ratio between the inner area $R_i$ and the outer radius $R_0$ (see FIG. 8). The ratio is varied between a range of 90% to 60% of $R_0$. The figure shows that the semicircular cross section provides higher moment of inertia which leads to higher stiffness of the torsional springs. It also shows that $I_3$ is max at ξ=73% which will be used as constant ratio $$\xi = \frac{R_i}{R_0}.$$

FIG. 8 shows the relation between the moment of inertia of different hollow cross sections with range of ratios of the inner and outer dimensions. The graphs show that the semicircular cross section maintains larger I and which ratio leads to larger I.

The load acting on the left and right segments is the grip force for an individual finger [Massy-Westropp, N. M., et al., Hand Grip Strength: age and gender stratified normative data in a populationbased study. BMC research notes, 2011. 4(1): p. 127]. The load is preferably larger than the pressure force acting inside the tube to guarantee the spraying action. The pressure force can be calculated using the Bernoulli equation (15) where the required parameter for the spray mechanism is the orifice diameter (nozzle exit, $R_e$) [Menon, E. S., Transmission pipeline calculations and simulations manual. 2015, Waltham, Mass.: Elsevier/Gulf Professional. xii, 599].

$$q = A_2\left[\frac{2(p_1 - p_2)}{\rho\left(1 - \left(\frac{A_2}{A_1}\right)^2\right)}\right]^{\frac{1}{2}} \quad (15)$$

Where q is the flow rate inside the delivery tubes in the pressure arm, $p_2$ and $A_2$, $p_1$ and $A_1$ are the pressure and the cross section area of at the orifice and the pressure arm respectively. From the Bernoulli equation, the orifice radius can be found based of the ratio (β) of the orifice radius ($R_e$) to the pressure arm inner radius ($R_0$).

$$\beta = \frac{R_e}{R_0} \quad (16)$$

The ratio (β) has a typical value that ranges from 0.3 to 0.75 depending of the required exit velocity [Upp, E. L. and P. J. LaNasa, Fluid flow measurement: a practical guide to accurate flow measurement. 2nd ed. 2002, Boston: Gulf Professional Pub. x, 264]. For the spray mechanism, the exit velocity should be in rage to ensure spraying action which does not require high speed. In some embodiments, the ratio (β) is 0.10 to 0.70, preferably 0.15 to 0.65, preferably 0.20 to 0.60, preferably 0.25 to 0.55, preferably 0.30 to 0.50, preferably 0.325 to 0.475, preferably 0.35 to 0.45, preferably 0.375 to 0.425, preferably 0.39 to 0.41, preferably 0.40.

In some embodiments, the compressible chamber has a hemispherical shape. Such embodiments are depicted in FIGS. 4A and 4B. In some embodiments, the hemispherical shape has an inner radius and an outer radius. In some embodiments, a ratio of the inner radius to the outer radius is 0.6 to 0.9, preferably 0.625 to 0.875, preferably 0.65 to 0.85, preferably 0.675 to 0.825, preferably 0.7 to 0.8, preferably 0.71 to 0.875, preferably 0.72 to 0.85, preferably 0.725 to 0.735, preferably 0.73.

In some embodiments, the spray mechanism is located on one or more finger areas of the palmar side of a glove or mitt. In general, the glove or mitt may be made of any suitable material or combination of materials known to one of ordinary skill in the art. In preferred embodiments, the glove is made from materials which do not harbor live microbes for extended periods of time [WebMD. Coronavirus and Surfaces: How Long Does COVID-19 Live on Surfaces? 2020 May 20 Available from: https://www.webmd.com/lung/how-long-covid-19-lives-on-surfaces]. Examples of such materials are nitrile, latex, vinyl, polyvinyl chloride, neoprene, and isoprene.

In some embodiments, the spray mechanism is reversibly connected to the glove such that the spray mechanism may be removed, a portion of the glove may be replaced, and the spray mechanism may be reattached. In such embodiments, the spray mechanism may be attached by any suitable reversible attachment mechanism known to one of ordinary skill in the art. Examples of such attachment mechanisms include hook and loop fasteners, snap-fit joints, adhesives, and straps. In some embodiments, the spray mechanism comprises loops or slots through which belts or straps may be passed. In such embodiments, the belts or straps are then used to secure the spray mechanism to the glove. In such embodiments, the belts or straps are adjustable, allowing for a secure fit to a hand, finger, or other appendage donning the glove. Such a secure fit may be advantageous for user comfort or effective operation of the spray mechanism. In alternative embodiments, the spray mechanism is attached to the glove by snap-fit joints. Snap-fit joints are a type of fitting in which one part is fitted with a small protrusion (e.g. hook, stud, or bead) which is deflected during assembly to catch in a depression on the mating part. In one example of snap-fit-containing embodiments, the glove comprises small protrusions which securely fit into small indentations on the spray mechanism. The secure fit provided by the protrusions and indentations ensure that the spray mechanism does not come detached during normal operation of the spray mechanism and/or glove but also that the spray mechanism may be removed by deliberate action.

In some embodiments, the spray mechanism is attached to the palm area of the palmar side of the glove or mitt. In alternative embodiments, the spray mechanism is attached to one or more finger areas of the palmar side of the glove or mitt. In such embodiments, the spray mechanism may be attached to an area which is defined by only one finger. Alternatively, the spray mechanism may be attached to an area defined by more than one finger. In such embodiments, the glove or mitt may have individual finger spaces or spaces which are configured to fit and house more than one finger. In such embodiments, such spaces may be configured to fit and house 2 fingers, 3 fingers, or 4 fingers. In such embodiments, such spaces preferably are not configured to fit or house the thumb. In preferred embodiments, the spray mechanism is attached to a finger area comprising at least one selected from the group consisting of the index finger, the middle finger, the ring finger, and the pinkie finger. In preferred embodiments, the spray mechanism is oriented and located such that the central segment is located on or about the middle phalanx area of the finger or fingers (i.e. between the distal interphalanx joint and the middle interphalanx joint). In such embodiments, one of the dispensing segments is located on or about the distal phalanx area (tip of the finger). In such embodiments, one of the dispensing segments is located on or about the proximal phalanx area (base of the finger).

In some embodiments, the spray mechanism has a length of 0.25 to 10 inches, preferably 0.5 to 8 inches, preferably 0.75 to 6 inches, preferably 1 to 5 inches, preferably 1.25 to 4.5 inches, preferably 1.5 to 4 inches, preferably 1.75 to 3.5 inches. In some embodiments, the central segment makes up 10 to 70%, preferably 15 to 65%, preferably 20 to 60%, preferably 22.5 to 55%, preferably 25 to 50%, preferably 27.5 to 45%, preferably 30 to 40% of the length of the spray mechanism. In some embodiments, the remaining length of the spray mechanism is made up of the joints and the dispensing segments. In some embodiments, the dispensing segments are of equal length. In alternative embodiments, one dispensing segment has a larger length than the other dispensing segment. In some embodiments, the spray mechanism has a width of 0.1 to 5 inches, preferably 0.25 to 4.5 inches, preferably 0.33 to 4 inches, preferably 0.5 to 3.5 inches, preferably 0.66 to 3 inches, preferably 0.75 to 2.5 inches.

Figure 9:
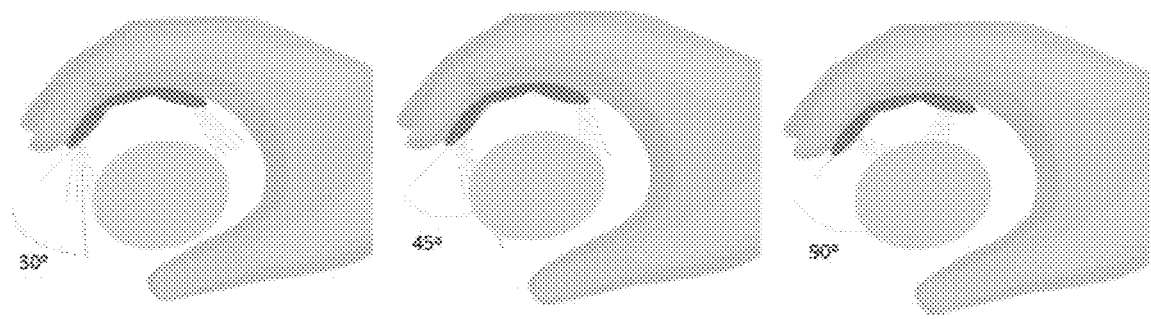
FIG. 9 shows a depiction of the coverage of an object with a spray of sanitizer solution from the spray mechanism for different spray angles without the sanitizer dispensing glove making contact with the object.

In some embodiments, the flexing of the spray mechanism and subsequent dispensing of sanitizer is caused by the flexing or closing of a hand, finger, or other appendage wearing the sanitizer dispensing glove. In some embodiments, the sanitizer dispensing glove is configured to dispense sanitizer solution onto an object as a result of the action of grasping said object. In preferred embodiments, the sanitizer dispensing glove is configured to dispense sanitizer solution onto an object without making contact with said object. An exemplary embodiment is shown in FIG. 9.

In general, the spray mechanism may be constructed of any suitable material or mixture of materials known to one of ordinary skill in the art. Examples of such suitable materials include, but are not limited to polydimethylsiloxane (PDMS), polylactic acid (PLA), acrylonitrile butadiene styrene (ABS) plastic, polycarbonate, polyethylene, EPDM, and ethylene vinyl acetate. In preferred embodiments, the entirety of the spray mechanism is constructed of a single material. In some embodiments, the entirety of the spray mechanism is constructed of a single piece of material. In general, the spray mechanism may be constructed using any technique known to one of ordinary skill in the art. Examples of such techniques include, but are not limited to injection molding, blow molding, CNC milling, stereolithography 3D printing, selective laser sintering (SLS), fused deposition modeling (FDM), digital light process (DLP) 3D printing, multi jet fusion (MJF) 3D printing, direct metal laser sintering (DMLS), and electron beam melting (EBM) 3D printing. For examples of suitable materials and method of constructing the spray mechanism, see Lateş, et. al. [Lateş, D., M. Căşvean, and S. Moica, Fabrication methods of compliant mechanisms. Procedia Engineering, 2017. 181: p. 221-225; & FORMLABS MATERIAL PROPERTIES—FLEXIBLE: Photopolymer Resin for Form 2 3D Printers. 2017; Available from: https://formlabs.com/materials/engineering/#flexible-resin].

The sanitizer dispensing glove also comprises a sanitizer solution reservoir. The sanitizer solution reservoir houses a volume of sanitizer solution which may be dispensed by the glove. The sanitizer dispensing glove also comprises a replenishment tube, fluidly connected to the sanitizer solution reservoir and the compressible chamber. The replenishment tube is preferably attached to, integral with, embedded within, or otherwise hidden by the glove material. The replenishment tube allows sanitizer solution to flow from the sanitizer reservoir to the compressible chamber. In some embodiments, said flow occurs during the relaxing of the spray mechanism from the compressed state to the relaxed state. In some embodiments, said flow refills the compressible chamber with sanitizer solution. In some embodiments, the sanitizer dispensing glove further comprises a replenishment one-way valve (also known as a check valve) located between the compressible chamber and the replenishment tube. In some embodiments, the replenishment one-way valve is oriented to allow an inflow of sanitizer solution from the replenishment tube into the compressible chamber and prevent an outflow of sanitizer solution from the compressible chamber into the replenishment tube. In some embodiments, the sanitizer dispensing glove further comprises a delivery one-way valve located between the compressible chamber and each delivery tube. In some embodiments, the delivery one-way valve is oriented to allow a flow of sanitizer solution from the compressible chamber to the delivery tube and prevent a backflow of sanitizer solution and/or air from the delivery tube to the compressible chamber.

In some embodiments, the sanitizer reservoir is attached to the glove or mitt. In some embodiments, the sanitizer reservoir is attached to an opisthenar surface of the glove or mitt. Such placement may prevent the sanitizer reservoir from interfering with a closing of a hand or other appendage donning the glove of mitt. In some embodiments, the sanitizer reservoir is located at or near a wrist portion of the glove. In such embodiments, the sanitizer reservoir may be located on either a palmar or opisthenar surface of the glove or mitt. In some embodiments, the sanitizer reservoir is not attached to the glove or mitt. In such embodiments, the replenishment tube has a glove-attached portion which is attached to, integral with, embedded within, or otherwise hidden by the glove material and a non-glove-attached portion which is not attached to, integral with, embedded within, or otherwise hidden by the glove material. In such embodiments, the sanitizer reservoir may be configured to be attached to a forearm, upper arm, waist, chest, back, thigh, or other area of a user's body. Such attachment may be achieved by a variety of attachment mechanisms or accessories. Examples of such attachment mechanisms or accessories include straps, clips, ties, buckles, snaps, buttons, and zippers. In one example, the sanitizer reservoir has a belt or strap which passes through loops on the exterior of the sanitizer reservoir which may secure the sanitizer reservoir to the forearm or upper arm. In another example, the sanitizer reservoir has a clip which allows the sanitizer reservoir to be attached to a belt worn by a user. In another example, the sanitizer reservoir has a strip of a hook-and-loop fastener material (i.e. either the hook material or the loop material) adhered to a surface of the sanitizer reservoir which allows the sanitizer reservoir to be attached to a strop of hook-and-loop fastener material on an article of clothing worn by a user.

In some embodiments, the sanitizer reservoir is otherwise sealed except for the connection to the replenishment tube. In such embodiments, the sanitizer reservoir may be pressurized. In such embodiments where the sanitizer reservoir is pressurized, the internal pressure of the sanitizer reservoir is sufficient to deliver the totality or an appropriate portion of the volume of sanitizer contained therein. In alternative embodiments, the sanitizer reservoir has an air inlet. The air inlet provides an inflow of air into the sanitizer reservoir such that a vacuum is not created as sanitizer solution is drained from the sanitizer reservoir by use of the spray mechanism. In such embodiments, the air inlet comprises a one-way valve. The air inlet one-way valve is oriented such that air may flow into the sanitizer reservoir, but sanitizer solution may not flow out of the sanitizer reservoir. In some embodiments, the sanitizer reservoir further comprises a refill port. The refill port is an opening through which the sanitizer reservoir may be refilled with sanitizer solution. In alternative embodiments, the sanitizer reservoir is designed to be discarded after being emptied or depleted of sanitizer solution. In such embodiments, the replenishment tube is configured to be detached from the sanitizer reservoir and attached to a replacement sanitizer reservoir.

In general, the sanitizer reservoir may be constructed of any suitable material known to one of ordinary skill in the art. Examples of such materials include, but are not limited to aluminum, stainless steel, acrylonitrile butadiene styrene (ABS) plastic, silicone rubber, polydimethylsiloxane (PDMS) polyvinyl chloride (PVC), polypropylene, polyethylene, polycarbonate plastic, polyethylene terephthalate (PET), nylon, polylactic acid (PLA), and polymethyl methacrylate (PMMA).

In some embodiments, the sanitizer reservoir has an interior volume of 1 to 1000 mL, preferably 5 to 900 mL, preferably 7.5 to 800 mL, preferably 10 to 750 mL, preferably 12.5 to 500 mL, preferably 15 to 500 mL, preferably 17.5 to 400 mL, preferably 20 to 350 mL, preferably 25 to 300 mL, preferably 30 to 250 mL, preferably 35 to 225 mL, preferably 40 to 200 mL, preferably 50 to 150 mL. In some embodiments, the sanitizer reservoir is rigid such that the interior volume does not change as sanitizer solution is drained from the sanitizer reservoir. In alternative embodiments, the sanitizer reservoir is flexible. In such embodiments, the sanitizer reservoir may contract or shrink as sanitizer solution is drained from the sanitizer reservoir. In such embodiments, the volume of the sanitizer reservoir may decrease so as to not allow a vacuum to be created in the sanitizer reservoir.

The present disclosure also relates to a method of sanitizing an object. The method comprises spraying onto said object a sanitizer solution by flexing or closing a hand, finger, or other appendage wearing the sanitizer dispensing glove as described above. In preferred embodiments, the spraying occurs without any portion of the sanitizer dispensing glove making contact with the object.

In some embodiments, the sanitizer solution comprises a disinfectant. As used herein, a disinfectant is a chemical agent that inactivates or destroys microbes that may be present on surfaces. Disinfectants are generally distinguished from other antimicrobial agents such as antibiotics, which inactivate or kill microbes within a body, and antiseptics, which inactivate or destroy microbes on living tissue. As used herein, "microbe" refers to a microorganism including, but not limited to archae, bacteria, protozoa, and viruses. The term microbe may be used to specifically refer to harmful or infectious microorganisms. In some embodiments, the sanitizing is a disinfecting. As defined by the US Environmental Protection Agency, sanitizing refers to reducing the amount of bacteria on a surface, typically by 99% or more, while disinfecting inactivates or destroys a wider range of microbes, including viruses. Examples of disinfectants include, but are not limited to alcohols such as ethanol and isopropanol, phenolics such as phenol, o-phenylphenol, chloroxylenol, and thymol, hydrogen peroxide, peroxy and peroxo acids such as peroxyformic acid, peracetic acid, peroxybenzoic acid, and peroxymonosulfuric acid, quaternary ammonium compounds such as benzalkonium chloride, cetrimoniium, and tetraethylammonium bromide, sodium hypochlorite, sodium percarbonate, and tetraacetyl ethylenediamine.

In preferred embodiments, the method kills, inactivates, or denatures greater than 97.5%, preferably greater than 98%, preferably greater than 98.5%, preferably greater than 99%, preferably greater than 99.25%, preferably greater than 99.5%, preferably greater than 99.75%, preferably greater than 99.9% of microbes present on the object before sanitizing.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A sanitizer dispensing glove, comprising:
a spray mechanism attached to or disposed upon a palmar side of a glove or mitt, the spray mechanism comprising;
   a pair of dispensing segments comprising a plurality of nozzles attached to, disposed upon, or formed from a material of the dispensing segments, and one or more delivery tubes connected to the nozzles, and
   a central segment located between and flexibly connected to the pair of dispensing segments by joints comprising pressure arms, the central segment comprising a compressible chamber fluidly connected to the delivery tubes;
a sanitizer solution reservoir;
a replenishment tube, fluidly connected to the sanitizer solution reservoir and the compressible chamber,
wherein the spray mechanism is configured to flex from a relaxed state to a compressed state and relax from a compressed state to a relaxed state.

2. The sanitizer dispensing glove of claim 1, wherein flexing of the spray mechanism from the relaxed state to the compressed state causes a compression of the compressible chamber which in turn causes an outflow of sanitizer solution housed in the compressible chamber into the delivery tubes and subsequently out through the nozzles as a spray, and relaxing of the spray mechanism from the compressed state to the relaxed state causes a decompression of the compressible chamber and subsequently an inflow of sanitizer solution from the sanitizer solution reservoir to the compressible chamber via the replenishment tube.

3. The sanitizer dispensing glove of claim 1, wherein:
the dispensing segments are substantially coplanar when in the relaxed state, having a dispensing segment angle, formed by the dispensing segments and central segment having the compressible chamber at the vertex of said angle, of 180 to 160°; and
the dispensing segments are substantially non-coplanar in the compressed state, having a dispensing segment angle of less than 160°.

4. The sanitizer dispensing glove of claim 1, wherein the nozzles are oriented so as to provide a spray of sanitizer solution in a cone shape having a cone angle of 15 to 115°.

5. The sanitizer dispensing glove of claim 4, wherein a spray angle between a midpoint of the cone shape of the spray of sanitizer solution and the dispenser segment from which the spray originated is 30 to 90°.

6. The sanitizer dispensing glove of claim 1, further comprising a replenishment one-way valve located between the compressible chamber and the replenishment tube.

7. The sanitizer dispensing glove of claim 6, wherein the replenishment one-way valve is oriented to allow an inflow of sanitizer solution from the replenishment tube into the compressible chamber and prevent an outflow of sanitizer solution from the compressible chamber into the replenishment tube.

8. The sanitizer dispensing glove of claim 1, further comprising a delivery one-way valve located between the compressible chamber and each delivery tube.

9. The sanitizer dispensing glove of claim 8, wherein the delivery one-way valve is oriented to allow a flow of sanitizer solution from the compressible chamber to the delivery tube and prevent a backflow of sanitizer solution and/or air from the delivery tube to the compressible chamber.

10. The sanitizer dispensing glove of claim 1, wherein the spray mechanism is located on one or more finger areas of the palmar side of the glove or mitt.

11. The sanitizer dispensing glove of claim 10, wherein the spray mechanism is removably attached to the finger area or areas.

12. The sanitizer dispensing glove of claim 1, wherein the spray mechanism is configured to flex and subsequently dispense sanitizer solution in response to flexing or closing of a hand, finger, or other appendage wearing the sanitizer dispensing glove.

13. The sanitizer dispensing glove of claim 12, wherein the sanitizer dispensing glove is configured to dispense sanitizer solution onto an object in response to grasping of said object.

14. The sanitizer dispensing glove of claim 12, wherein the sanitizer dispensing glove is configured to dispense sanitizer solution onto an object without making contact with said object.

15. A method of sanitizing an object comprising spraying onto said object a sanitizer solution by flexing or closing a hand, finger, or other appendage wearing the sanitizer dispensing glove of claim 1.

16. The method of claim 15, wherein the spraying occurs without any portion of the sanitizer dispensing glove making contact with the object.

17. The method of claim 15, wherein the sanitizer solution comprises a disinfectant.

18. The method of claim 15, wherein the method kills greater than 97.5% of microbes present on the object before sanitizing.

* * * * *